United States Patent
Gross

(10) Patent No.: US 8,273,063 B2
(45) Date of Patent: Sep. 25, 2012

(54) IMPLANTABLE PUMP FOR DRUG DELIVERY TO TREAT ERECTILE DYSFUNCTION

(76) Inventor: Yossi Gross, Moshav Mazor (IL)

( * ) Notice: Subject to any disclaimer, the term of this patent is extended or adjusted under 35 U.S.C. 154(b) by 749 days.

(21) Appl. No.: 12/227,763

(22) PCT Filed: May 30, 2007

(86) PCT No.: PCT/IL2007/000653
§ 371 (c)(1),
(2), (4) Date: Feb. 17, 2009

(87) PCT Pub. No.: WO2007/138590
PCT Pub. Date: Dec. 6, 2007

(65) Prior Publication Data
US 2010/0145299 A1   Jun. 10, 2010

Related U.S. Application Data

(60) Provisional application No. 60/803,414, filed on May 30, 2006.

(51) Int. Cl.
*A61M 37/00* (2006.01)
(52) U.S. Cl. .............................. 604/288.01
(58) Field of Classification Search .......... 604/892.1, 604/890.1, 891.1, 27, 30, 31, 33, 65–67, 604/246, 247, 248, 212–216, 153, 156, 19, 604/20, 93.01, 288.01; 600/9, 12, 29, 30
See application file for complete search history.

(56) References Cited

U.S. PATENT DOCUMENTS

| | | | |
|---|---|---|---|
| 3,416,532 A | 12/1968 | Grossman | |
| 3,827,426 A | 8/1974 | Page et al. | |
| 3,885,251 A | 5/1975 | Pedroso | |
| 4,829,990 A | 5/1989 | Thuroff et al. | |
| 4,982,731 A | 1/1991 | Lue et al. | |
| 5,030,213 A * | 7/1991 | Rumberger et al. | 604/267 |
| 5,048,511 A * | 9/1991 | Rosenbluth et al. | 600/40 |
| 5,281,205 A | 1/1994 | McPherson | |
| 5,324,323 A | 6/1994 | Bui | |
| 5,328,460 A | 7/1994 | Lord et al. | |
| 5,372,573 A | 12/1994 | Habib | |

(Continued)

FOREIGN PATENT DOCUMENTS
EP       0109935       5/1984
(Continued)

OTHER PUBLICATIONS
International Search Report for international application PCT/IL2007/00653.

(Continued)

*Primary Examiner* — Manuel Mendez
(74) *Attorney, Agent, or Firm* — Husch Blackwell LLP

(57) ABSTRACT

An implantable pump (10) is provided for pumping a drug in a patient's body (100). The pump includes a drug delivery chamber (22) configured to be filled with the drug and a drug delivery catheter (50) having a catheter lumen (58) and a distal end (56), the drug delivery catheter in fluid communication with the drug delivery chamber and configured to deliver the drug to a delivery site (102). It also includes a pushing element (44) coupled to the distal end of the catheter, and configured to push away from the catheter lumen fibrotic matter that has developed in response to the drug delivery catheter. Other embodiments are also described.

27 Claims, 3 Drawing Sheets

U.S. PATENT DOCUMENTS

| | | | |
|---|---|---|---|
| 5,611,767 A * | 3/1997 | Williams | 600/2 |
| 5,645,839 A | 7/1997 | Chobanian et al. | |
| 5,800,502 A | 9/1998 | Boutos | |
| 5,900,433 A | 5/1999 | Igo et al. | |
| 5,904,712 A | 5/1999 | Axelgaard | |
| 6,023,640 A | 2/2000 | Ross | |
| 6,038,485 A | 3/2000 | Axelgaard | |
| 6,058,331 A | 5/2000 | King | |
| 6,086,527 A | 7/2000 | Talpade | |
| 6,190,352 B1 * | 2/2001 | Haarala et al. | 604/93.01 |
| 6,200,259 B1 | 3/2001 | March | |
| 6,347,247 B1 | 2/2002 | Dev et al. | |
| 6,463,323 B1 | 10/2002 | Conrad-Vlasak et al. | |
| 6,554,822 B1 * | 4/2003 | Holschneider et al. | 604/892.1 |
| 6,679,832 B1 | 1/2004 | Sultan | |
| 6,706,682 B2 | 3/2004 | Shabsigh | |
| 6,725,492 B2 | 4/2004 | Moore et al. | |
| 6,810,286 B2 | 10/2004 | Donovan et al. | |
| 6,824,561 B2 | 11/2004 | Soykan et al. | |
| 6,845,267 B2 | 1/2005 | Harrison et al. | |
| 6,865,416 B2 | 3/2005 | Dev et al. | |
| 6,871,092 B2 | 3/2005 | Piccone et al. | |
| 6,885,895 B1 | 4/2005 | Whitehurst et al. | |
| 6,939,345 B2 | 9/2005 | KenKnight et al. | |
| 7,206,637 B2 | 4/2007 | Salo | |
| 7,229,403 B2 | 6/2007 | Schock et al. | |
| 2002/0103454 A1 | 8/2002 | Sackner et al. | |
| 2003/0036773 A1 | 2/2003 | Whitehurst et al. | |
| 2003/0204206 A1 | 10/2003 | Padua et al. | |
| 2004/0039417 A1 | 2/2004 | Soykan et al. | |
| 2004/0106954 A1 | 6/2004 | Whitehurst et al. | |
| 2005/0240229 A1 | 10/2005 | Whitehurst et al. | |
| 2006/0235263 A1 * | 10/2006 | Jacobson et al. | 600/31 |
| 2006/0276844 A1 | 12/2006 | Alon et al. | |

FOREIGN PATENT DOCUMENTS

| | | |
|---|---|---|
| WO | WO 84/01905 | 5/1984 |
| WO | WO 2004/014456 | 2/2004 |
| WO | WO 2005/074384 | 8/2005 |
| WO | WO 2006/064503 | 6/2006 |
| WO | WO 2006/094273 | 9/2006 |
| WO | WO 2006/123346 | 11/2006 |
| WO | WO 2007/013065 | 2/2007 |
| WO | WO 2007/064895 | 6/2007 |
| WO | WO 2007/106533 | 9/2007 |
| WO | WO 2007/113833 | 10/2007 |

OTHER PUBLICATIONS

"A Miniature Peristaltic Pump with Electronic Rate Control: Technical Adaptation to a Clinical need", by Ball G et al., Biomed Eng. Dec. 1974; 9(12):563-5.

* cited by examiner

IMPLANTABLE PUMP FOR DRUG DELIVERY TO TREAT ERECTILE DYSFUNCTION

CROSS-REFERENCES TO RELATED APPLICATIONS

The present application is a U.S. national phase of PCT Application No. PCT/IL2007/000653 to Gross, filed May 30, 2007, which claims the benefit of U.S. Provisional Patent Application 60/803,414 to Gross, filed May 30, 2006, which is incorporated herein by reference.

FIELD OF THE INVENTION

The present invention relates to implantable medical apparatus. Specifically, the present invention relates to methods and apparatus for treating erectile dysfunction.

BACKGROUND OF THE INVENTION

As set forth in U.S. Patent Application Publication No. 2005/0240229, which is incorporated herein by reference, a large number of men suffer erectile dysfunction to a greater or lesser degree. Erectile dysfunction etiologies include neuropathy and vascular disease. The male erectile response is initiated by the action of neurons, or nerve cells (i.e., neuronal action), and is maintained by a complex interplay between events involving blood vessels (i.e., vascular events) and events involving the nervous system (i.e., neurological events).

Male erectile dysfunction has a number of causes, both physiological and psychological, and in many patients the disorder may be multifactorial. Several causes are essentially neurologic in origin. Damage to the spinal cord may produce varying degrees of erectile failure depending on the location and severity of the damage. Damage to the pathways used by the autonomic nervous system to innervate the penis may interrupt psychogenic erection initiated by the central nervous system. Damage to somatic nervous pathways may impair reflexogenic erections and may interrupt tactile sensation needed to maintain psychogenic erections. Not only do traumatic lesions affect erectile ability, but also disorders leading to peripheral neuropathy may impair neuronal innervation of the penis or of the sensory afferents. The endocrine system itself, particularly the production of androgens, appears to play a role in regulating sexual interest, and may also play a role in erectile function. Erectile dysfunction is also a common complication of prostate surgery, such as prostatectomy (surgical removal of all or part of the prostate), which is a mainstay of treatment for prostate cancer.

The oral antipressor agent, sildenafil citrate (available from Pfizer, Inc. of New York, N.Y., under the trademark VIAGRA), is clinically available for treatment of male erectile dysfunction. An oral dose typically requires an hour to achieve full effect. The agent may have side effects such as abnormal vision, flushing, headache, and diarrhea, however, the ability to preserve erectile function following prostate surgery has been favorably affected by the availability of sildenafil. Sildenafil appears to be most effective when there is some remaining erectile function.

In intracavernosal injection therapy, the patient injects vasodilator agents (e.g., alprostadil, papaverine, phentolamine) directly into the corpora of the penis, thus avoiding undesirable systemic effects of the agent. The most commonly used drug is alprostadil, a naturally occurring prostaglandin, which is present in the penis and is involved in the natural erection process. Alprostadil relaxes the blood vessels and muscles in the erectile tissue of the penis allowing increased blood flow, the basis of a normal erection. However, a high rate of patient dropout occurs due to the unpleasant delivery mode.

Erectile dysfunction may also be treated transcutaneously at a site of concern using prostaglandins such as PGE or alprostadil, nitroglycerin, papaverine, yohimbine, sildenafil citrate, apomorphine HCI, and other known agents.

Implantable drug delivery pumps have been described for implantation in the scrotum or subcutaneously in the abdominal region. Such pumps store a vasoactive agent (e.g., a vasodilator), and provide a mechanism for delivering a bolus of the stored agent into the corpus cavernosum. See, for example, the description of various implantable drug pumps set forth in U.S. Pat. No. 6,679,832', which is incorporated herein by reference, and references cited therein. Generally, such implantable drug pumps comprise a refillable fluid agent storage chamber, a pump mechanism for delivering the bolus of agent from the storage chamber, and a catheter extending from the pump mechanism to deliver the agent to the site in the corpus cavernosum. The pump mechanism may be manually actuated by the patient to deliver a bolus of vasoactive agent.

As noted in U.S. Pat. No. 5,328,460, which is incorporated herein by reference, implanting a pump in a patient may trigger tissue growth encapsulating substantially the entire distal end of the catheter and blocking the lumen end opening or intruding into and thereby blocking or occluding the catheter lumen and inhibiting the delivery of medication. A mechanism for detecting such obstructions is proposed in the U.S. Pat. No. 5,328,460 patent.

SUMMARY OF THE INVENTION

Embodiments of the present invention provide apparatus and methods for countering blockage of the lumen end openings and occlusion of the lumen of an implanted drug pump. In certain embodiments, the apparatus and methods function each time that a bolus of drug is delivered.

In certain embodiments, the drug pump is adapted to be implanted to store a vasoactive agent for delivery through the drug delivery catheter to a site in the corpus cavernosum.

In certain embodiments, the drug pump comprises a delivery mechanism that may be manually actuated by the patient to deliver a bolus of vasoactive agent from a drug storage chamber through the drug delivery catheter while simultaneously clearing any blockage of the lumen end opening.

There is therefore provided, in accordance with an embodiment of the invention, an implantable pump for pumping a drug in a patient's body, including:

a drug delivery chamber configured to be filled with the drug;

a drug delivery catheter having a catheter lumen and a distal end, the drug delivery catheter in fluid communication with the drug delivery chamber and configured to deliver the drug to a delivery site; and a pushing element coupled to the distal end of the catheter, and configured to push away from the catheter lumen fibrotic matter that has developed in response to the drug delivery catheter.

In an embodiment, the pushing element is configured to prevent ingrowth of fibrotic matter to the catheter lumen by occluding the distal end of the catheter lumen when the pushing element is not pushing away fibrotic matter.

In an embodiment, the delivery site includes a site of a penis of the patient and the pump is configured to deliver the drug to the site of the penis of the patient.

In an embodiment, the delivery site includes a site of a corpus cavernosum of the patient and the pump is configured to deliver the drug to the site of the corpus cavernosum of the patient.

In an embodiment, the drug includes a vasoactive agent and the pump is configured to deliver the vasoactive agent to the site of the penis of the patient.

In an embodiment, the pump includes a drug storage chamber in fluid communication with the drug delivery chamber and configured to store the drug.

In an embodiment, the drug storage chamber is configured to expand during filling thereof with the drug.

In an embodiment, the pump includes a check valve configured to withhold a flow of the drug from the drug storage chamber to the drug delivery chamber responsively to a pressure difference between the drug storage chamber and the drug delivery chamber.

In an embodiment, the pump includes a needle, and the drug storage chamber includes a penetrable membrane, configured to be penetrated by the needle to facilitate delivery of the drug to the drug storage chamber while the drug storage chamber is within the patient.

In an embodiment, the pump includes an input device, configured to receive an input and, in response thereto, initiate delivery of a bolus of the drug from the drug delivery chamber through the catheter lumen to the delivery site.

In an embodiment, the pushing element is configured to push away the fibrotic matter each time that the input device receives the input.

In an embodiment, the input includes an input from the patient and the input device is configured to receive the input from the patient.

In an embodiment, the input device includes a push button.

There is also provided, in accordance with an embodiment of the invention, an implantable drug pump for implantation in a patient's body, including:

a drug delivery chamber adapted to be filled with a drug to be delivered to a drug delivery site in the patient's body;

a drug delivery catheter having a catheter lumen and extending from the drug delivery chamber to a delivery catheter distal end that is adapted to be disposed in the patient's body and that is prone to fibrin buildup;

means for initiating delivery of a bolus of the drug from the drug delivery chamber through the catheter lumen to the delivery site; and means for pushing a fibrin buildup away from the delivery catheter distal end.

The present invention will be more fully understood from the following detailed description of embodiments thereof, taken together with the drawings, in which:

DETAILED DESCRIPTION OF EMBODIMENTS

One application of the principles of the present invention involves an implantable drug pump configured to provide a vasoactive agent to a site in the corpus cavernosum to facilitate a male erection. An embodiment is described and illustrated in that context, but may have application in other drug or substance delivery implantable drug pump contexts.

Figure 1:
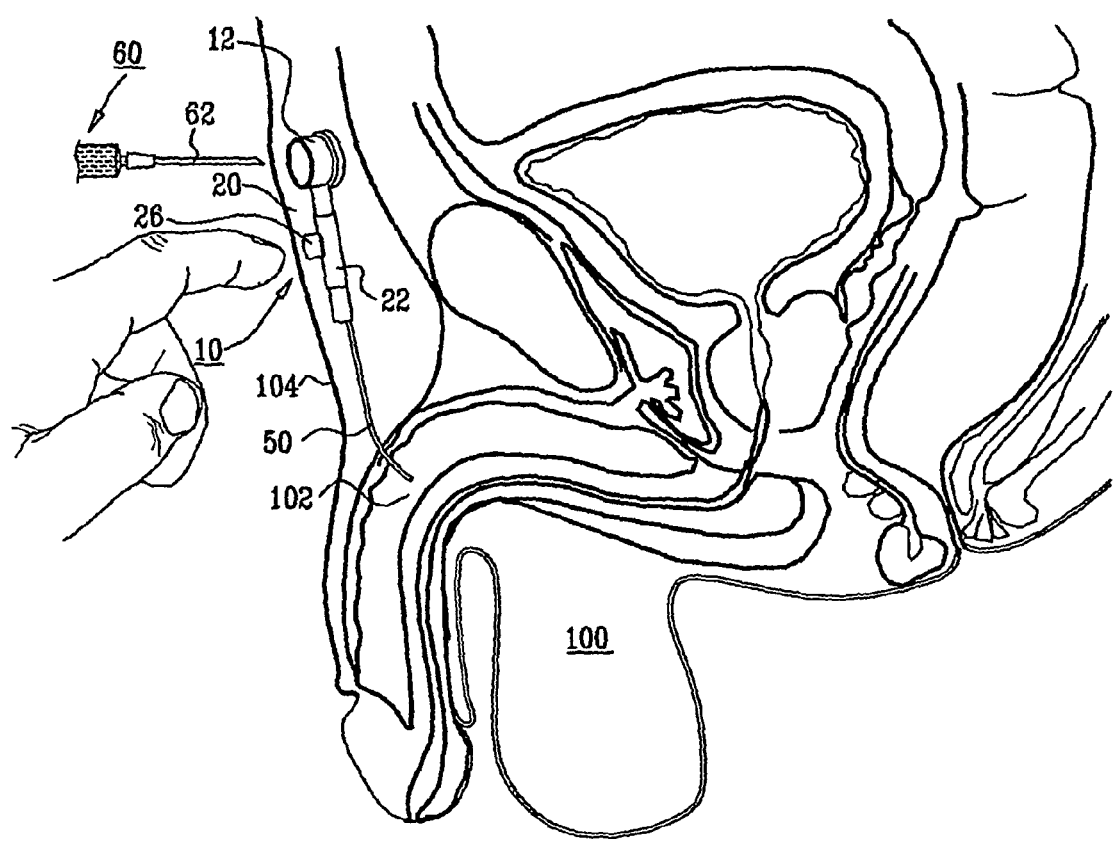
FIG. 1 is a schematic illustration of an implantable drug pump in accordance with an embodiment of the invention. The pump comprises a drug delivery catheter coupled by a drug delivery chamber to a drug storage chamber, for manually instigating the delivery of a bolus of vasoactive agent through the drug delivery catheter to a site in the corpus cavernosum.

The implantable drug pump 10 illustrated in FIGS. 1-5 comprises a drug delivery catheter 50 coupled by a drug delivery chamber 22 to a drug storage chamber 12 for manually instigating the delivery of a bolus of vasoactive agent through the drug delivery catheter 50 to a site in the corpus cavernosum 102 of a patient 100. The drug storage chamber 12 and drug delivery chamber 22 are typically joined together in a single unit and implanted subcutaneously in the abdominal region as shown in FIG. 1. The proximal end of drug delivery catheter 50 is joined to the drug delivery chamber 22. At its distal end, catheter 50 extends to the drug delivery site in the corpus cavernosum.

As shown in FIGS. 2-5, a drug pump housing 14 encloses the drug storage chamber 12 and a drug delivery chamber 22, the chambers being interconnected by a fluid channel including a check valve 18. A penetrable septum 16 covers the drug storage chamber 12. The septum 16 may be of the type that is penetrable by the needle 62 of a syringe 60 extended through the patient's skin 104 to fill the chamber 12 with the vasoactive agent and that is resealable upon withdrawal of the needle 62. The volume of the storage chamber 12 may be expandable by use of a bellows type chamber wall 120 coupled to the housing 14, so that the vasoactive agent is stored under pressure. During filling, the pressure of the vasoactive agent introduced into the storage chamber 12 overcomes the resistance of check valve 18, and passes vasoactive agent into the drug delivery chamber 22, so that the drug delivery chamber 22 and the drug storage chamber 12 are both filled with the vasoactive agent.

A drug delivery mechanism 20 is supported by housing 14 within the drug delivery chamber 22. Delivery mechanism 20 comprises a bar linkage 30, which functions as a pump actuator and which comprises links 32 and 34 and pivots 36, 38, and 40. One end of link 32 can pivot with respect to pivot 36 (fixed to housing 14), and the other end of link 32 and one end of link 34 can pivot with respect to pivot 38. The other end of link 34 is joined at pivot 40 to one end of shaft 42, which is movable along the length of the catheter lumen of drug delivery catheter 50 as described below.

The housing 14 also supports a drug delivery mechanism cover 26 filling an opening in the housing 14 of the drug delivery chamber 22. The cover 26 is formed of a resilient material, is thin in thickness, and is adapted to be positioned toward the patient's skin 104 when the drug pump 10 is implanted as shown in FIG. 1. The cover 26 is disposed over the pivot 38 of linkage 30, pivot 38 being biased to extend outward toward the cover 26 as shown in FIG. 2.

Figure 4:
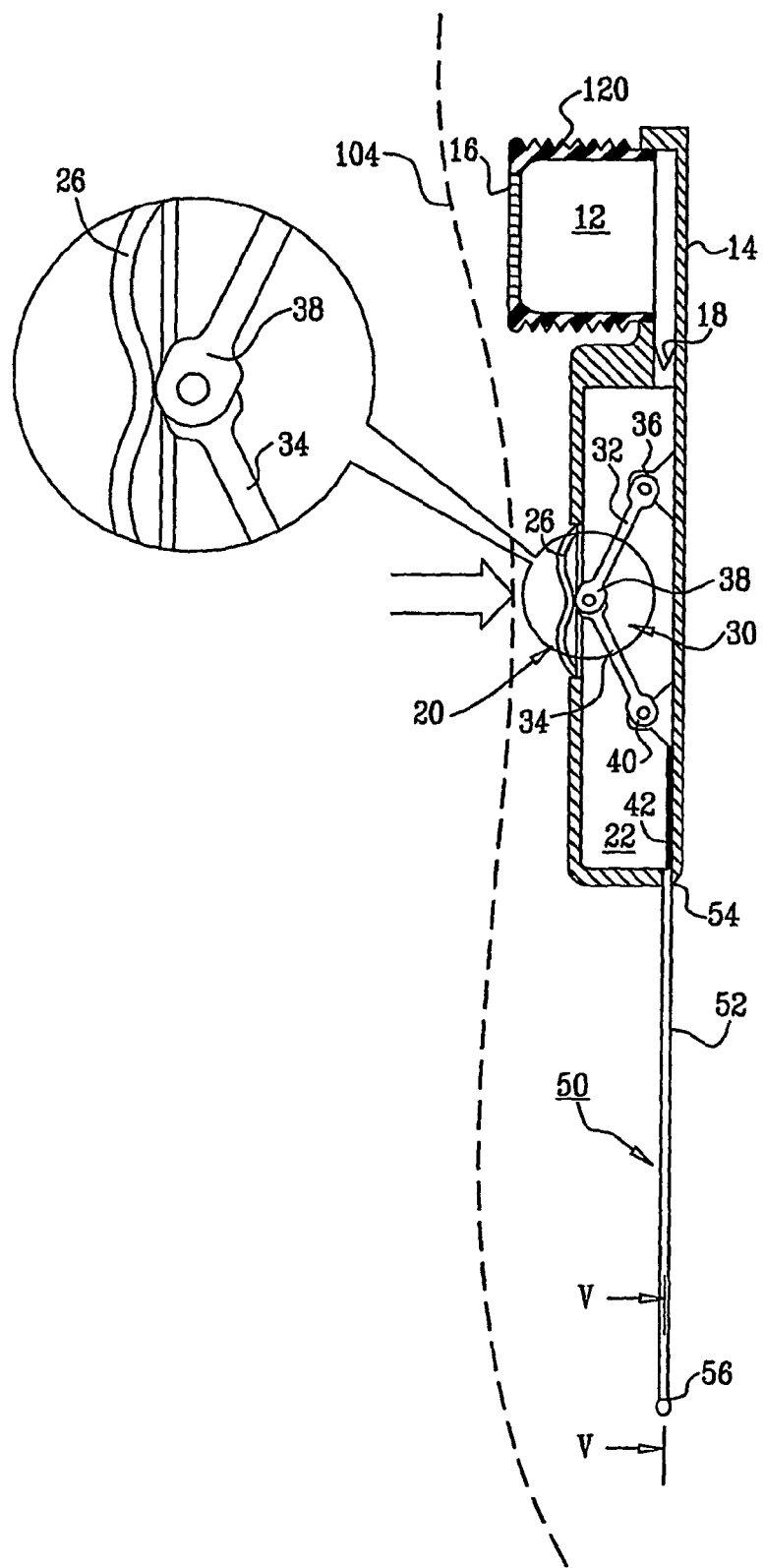
FIG. 4 is a cross-sectional view of the implantable drug pump of FIG. 1, illustrating the manual activation of a drug delivery mechanism to deliver a bolus of vasoactive agent from a drug delivery chamber through the drug delivery catheter while simultaneously clearing any blockage of the lumen end opening, in accordance with an embodiment of the present invention.

As shown in FIG. 4, the cover 26 may be depressed inward like a push button against the pivot 38 to move pivot 38 inward in drug delivery chamber 22. The inward movement of pivot 38 effects inward depression of links 32 and 34 and a longitudinal movement or separation of pivot 40 from pivot 36 because pivot 36 is fixed and pivot 40 is movable. The movement of pivot 40 effects distal movement of shaft 42 away from the housing 14.

Drug delivery catheter 50 comprises an elongated catheter body 52 enclosing a catheter lumen 58 extending between a catheter proximal end 54 coupled to housing 14 and a catheter distal end 56 adapted to be disposed at the drug delivery site. The shaft 42 extends from pivot 40 through the catheter lumen 58 to a cylindrical shaft distal end 44 depicted in FIGS. 3 and 5. The shaft 42 also passes through a resilient check valve 48 disposed in catheter lumen 58 proximal to the catheter distal end 56, so that the check valve 48 seals against the shaft 42.

Figure 2:
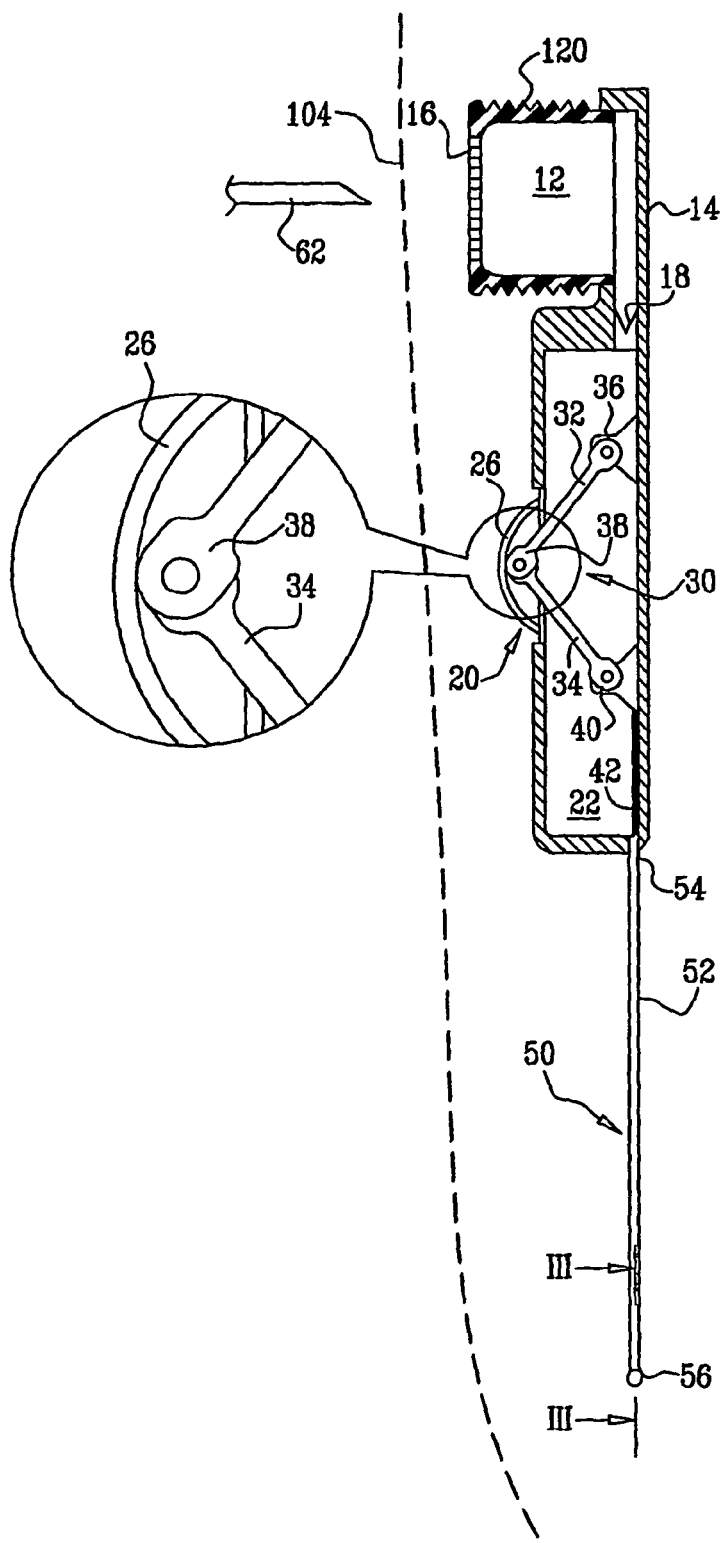
FIG. 2 is a cross-sectional view of the implantable drug pump of FIG. 1 illustrating the use of a syringe to fill the drug storage chamber with a vasoactive agent while the pump is not activated, in accordance with an embodiment of the present invention.
Figure 3:
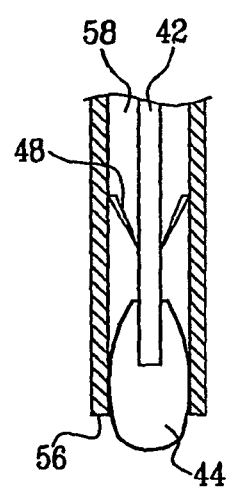
FIG. 3 is an expanded partial cross-sectional view of the distal end of the delivery catheter of FIG. 2, in accordance with an embodiment of the present invention.

The linkage 30 is disposed as shown in FIG. 2, and the shaft distal end 44 is retracted into catheter lumen 58 during filling of the chambers 12 and 22 as described above and as long as the patient does not depress the cover 26. In these states, the shaft distal end 44 is sized and shaped with respect to catheter lumen 58 to obstruct and to seal the distal lumen end opening from tissue ingrowth, as shown in FIG. 3. The catheter lumen 58 may be filled with vasoactive agent, but check valve 48 and shaft distal end 44 prevent its leakage through the distal lumen end opening.

Figure 5:
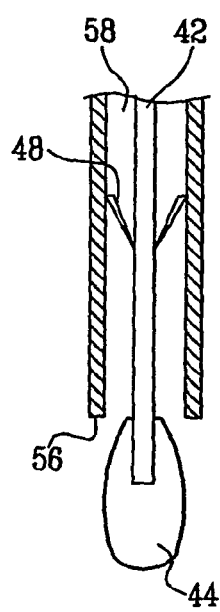
FIG. 5 is an expanded partial cross-sectional view of the distal end of the delivery catheter of FIG. 4, in accordance with an embodiment of the present invention.

Depression of the cover 26 by the patient, as shown in FIG. 4, causes the linkage 30 to move the shaft distal end 44 distally out of the distal lumen end opening as shown in FIG. 5, allowing vasoactive agent to escape from the catheter lumen 58. The depression of the cover 26 also decreases the volume of the drug delivery chamber 22 and pressurizes the drug acting on the check valve 48. The check valve 48 is overcome by the applied pressure so that a bolus of the vasoactive agent passes through the check valve 48 and out of the distal lumen end opening.

At the same time, the outward movement of the enlarged shaft distal end 44 can push away fibrotic matter that has grown around the distal lumen end opening which might otherwise impede delivery of the vasoactive agent.

The fluid pressure within the drug delivery chamber 22 is lowered upon delivery of the vasoactive agent and release of pressure applied to cover 26. Vasoactive agent stored in storage chamber 12 may then pass through the check valve 18 and into the drug delivery chamber 22. The patient may refill the drug storage chamber 12 from time to time.

It will be understood that the pump actuator may take other forms than linkage 30, e.g., a curved leaf spring fixed at one end to or bearing against one end of housing 14, fixed at the other end to the shaft 42, and bowed toward the cover 26.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An implantable pump for pumping a drug in a patient's body, comprising:

a drug delivery chamber configured to be filled with the drug;

a drug delivery catheter having a catheter lumen and a distal end, the drug delivery catheter in fluid communication with the drug delivery chamber and configured to deliver the drug to a delivery site; and a pushing element coupled to the distal end of the catheter, and configured to push away from the catheter lumen fibrotic matter that has developed in response to the drug delivery catheter.

2. The pump according to claim 1, wherein the pushing element is configured to prevent ingrowth of fibrotic matter to the catheter lumen by occluding a distal end of the catheter lumen when the pushing element is not pushing away fibrotic matter.

3. The pump according to claim 1, wherein the delivery site includes a site of a penis of the patient and the pump is configured to deliver the drug to the site of the penis of the patient.

4. The pump according to claim 3, wherein the delivery site includes a site of a corpus cavernosum of the patient and the pump is configured to deliver the drug to the site of the corpus cavernosum of the patient.

5. The pump according to claim 3, wherein the drug includes a vasoactive agent and the pump is configured to deliver the vasoactive agent to the site of the penis of the patient.

6. The pump according to claim 1, comprising a drug storage chamber in fluid communication with the drug delivery chamber and configured to store the drug.

7. The pump according to claim 6, wherein the drug storage chamber is configured to expand during filling thereof with the drug.

8. The pump according to claim 6, comprising a check valve configured to withhold a flow of the drug from the drug storage chamber to the drug delivery chamber responsively to a pressure difference between the drug storage chamber and the drug delivery chamber.

9. The pump according to claim 6, comprising a needle, wherein the drug storage chamber comprises a penetrable membrane, configured to be penetrated by the needle to facilitate delivery of the drug to the drug storage chamber while the drug storage chamber is within the patient.

10. The pump according to claim 1, comprising an input device, configured to receive an input and, in response thereto, initiate delivery of a bolus of the drug from the drug delivery chamber through the catheter lumen to the delivery site.

11. The pump according to claim 10, wherein the pushing element is configured to push away the fibrotic matter each time that the input device receives the input.

12. The pump according to claim 11, wherein the input includes an input from the patient and wherein the input device is configured to receive the input from the patient.

13. The pump according to 11, wherein the input device comprises a push button.

14. A method for operating an implantable drug pump implanted in a patient's body, comprising:

initiating delivery of a bolus of a drug to a delivery site within the patient's body, via a catheter; and pushing away, using a pushing element coupled to the distal end of the catheter, fibrotic matter that has developed in response to the drug pump.

15. The method according to claim 14, wherein pushing away the fibrotic matter comprises pushing away the fibrotic matter each time the delivery of the bolus of the drug is initiated.

16. The method according to claim 14, comprising preventing ingrowth of fibrotic matter to a lumen of the pump, by occluding the lumen of the pump when the bolus of the drug is not being delivered.

17. The method according to claim 14, wherein the delivery site includes a site of a penis of the patient, and wherein initiating the delivery of the bolus of the drug comprises initiating the delivery of the bolus of the drug to the site of the penis of the patient.

18. The method according to claim 17, wherein the delivery site includes a site of a corpus cavernosum of the patient, and wherein initiating the delivery of the bolus of the drug comprises initiating the delivery of the bolus of the drug to the site of the corpus cavernosum of the patient.

19. The method according to claim 17, wherein the drug includes a vasoactive agent, and wherein initiating the delivery of the bolus of the drug to the site of the penis of the patient comprises initiating the delivery of a bolus of the vasoactive agent to the site of the penis of the patient.

20. The method according to claim 14, comprising filling the drug pump with the drug while the drug pump is within the patient.

21. The method according to claim 20, wherein filling the drug pump with the drug comprises injecting the drug into the pump.

22. The method according to claim 14, wherein initiating delivery of the bolus of the drug comprises receiving an input and initiating delivery of the bolus of the drug in response thereto.

23. The method according to claim 22, wherein pushing away the fibrotic matter comprises receiving the input and pushing away the fibrotic matter in response thereto, at the same time as the delivery of the bolus of the drug is initiated.

24. The method according to claim 23, wherein receiving the input comprises receiving an input from the patient.

25. The method according to claim 23, wherein receiving the input comprises receiving an input via a push-button.

26. An implantable drug pump for implantation in a patient's body comprising:
    a drug delivery chamber adapted to be filled with a drug to be delivered to a drug delivery site in the patient's body;
    a drug delivery catheter having a catheter lumen and extending from the drug delivery chamber to a delivery catheter distal end that is adapted to be disposed in the patient's body and that is prone to fibrin buildup;
    means for initiating delivery of a bolus of the drug from the drug delivery chamber through the catheter lumen to the delivery site; and
    means for pushing, coupled to the delivery catheter distal end, and configured to push a fibrin buildup away from the delivery catheter distal end.

27. A method of operating an implantable drug pump of the type comprising a drug delivery chamber and a drug delivery catheter having a catheter lumen and extending from the drug delivery chamber to a delivery catheter distal end that is adapted to be disposed in a patient's body and that is prone to fibrin buildup when implanted in the patient's body, the method comprising:
    filling the drug delivery chamber with a drug to be delivered to a drug delivery site in the patient's body;
    initiating delivery of a bolus of the drug from the drug delivery chamber through the catheter lumen to the delivery site; and
    pushing a fibrin buildup away from the delivery catheter distal end, using a pushing element coupled to the delivery catheter distal end.

* * * * *